United States Patent [19]

Randolph

[11] 4,132,224

[45] Jan. 2, 1979

[54] DUROMETER FOR INDENTIBLE TISSUE AND THE LIKE

[76] Inventor: Robert G. Randolph, 4146 Howard Ave., Western Springs, Ill. 60558

[21] Appl. No.: 758,653

[22] Filed: Jan. 12, 1977

[51] Int. Cl.² .............................................. A61B 5/10
[52] U.S. Cl. ........................................ 128/2 S; 73/81
[58] Field of Search ............... 128/2 R, 2 S, 2 N, 2 T; 73/81, 141 A, 105

[56] References Cited

U.S. PATENT DOCUMENTS

| | | | |
|---|---|---|---|
| 1,549,115 | 8/1925 | Hancock | 73/81 |
| 2,372,662 | 4/1945 | Dewey | 73/81 |
| 2,460,726 | 2/1949 | Arndt, Jr. | 73/105 |
| 3,201,976 | 8/1965 | Starrett et al. | 73/81 |
| 3,934,463 | 1/1976 | Venderjagt | 73/81 |
| 3,956,924 | 5/1976 | Hansen et al. | 73/81 |

FOREIGN PATENT DOCUMENTS 311620  6/1972  U.S.S.R. .................................. 128/2 S

*Primary Examiner*—Lee S. Cohen
*Attorney, Agent, or Firm*—McCaleb, Lucas & Brugman

[57] ABSTRACT

A pair of parallel flexible beams, here illustrated as flat steel springs, extend forwardly from a handle. One end of one spring beam is formed at a right angle to provide a laterally-extending tissue-engageable indentor which passes through, and extends beyond a forked opening in the end of the other spring beam. Separate strain gages are mounted on the spring beams. When the indentor is pressed into tissue, deflection of the indentor beam is determined by change in electrical characteristics of the corresponding strain gage through a bridge circuit and is indicated in a digital read-out display on the handle. When the indentor beam deflects sufficiently for the end of the forked beam to contact the tissue, and begin to deflect, the resulting change in electrical characteristics of the strain gage on the forked beam generates a lock signal which "freezes" or locks the reading in the read-out display as of the time of initial deflection of the forked beam.

16 Claims, 3 Drawing Figures

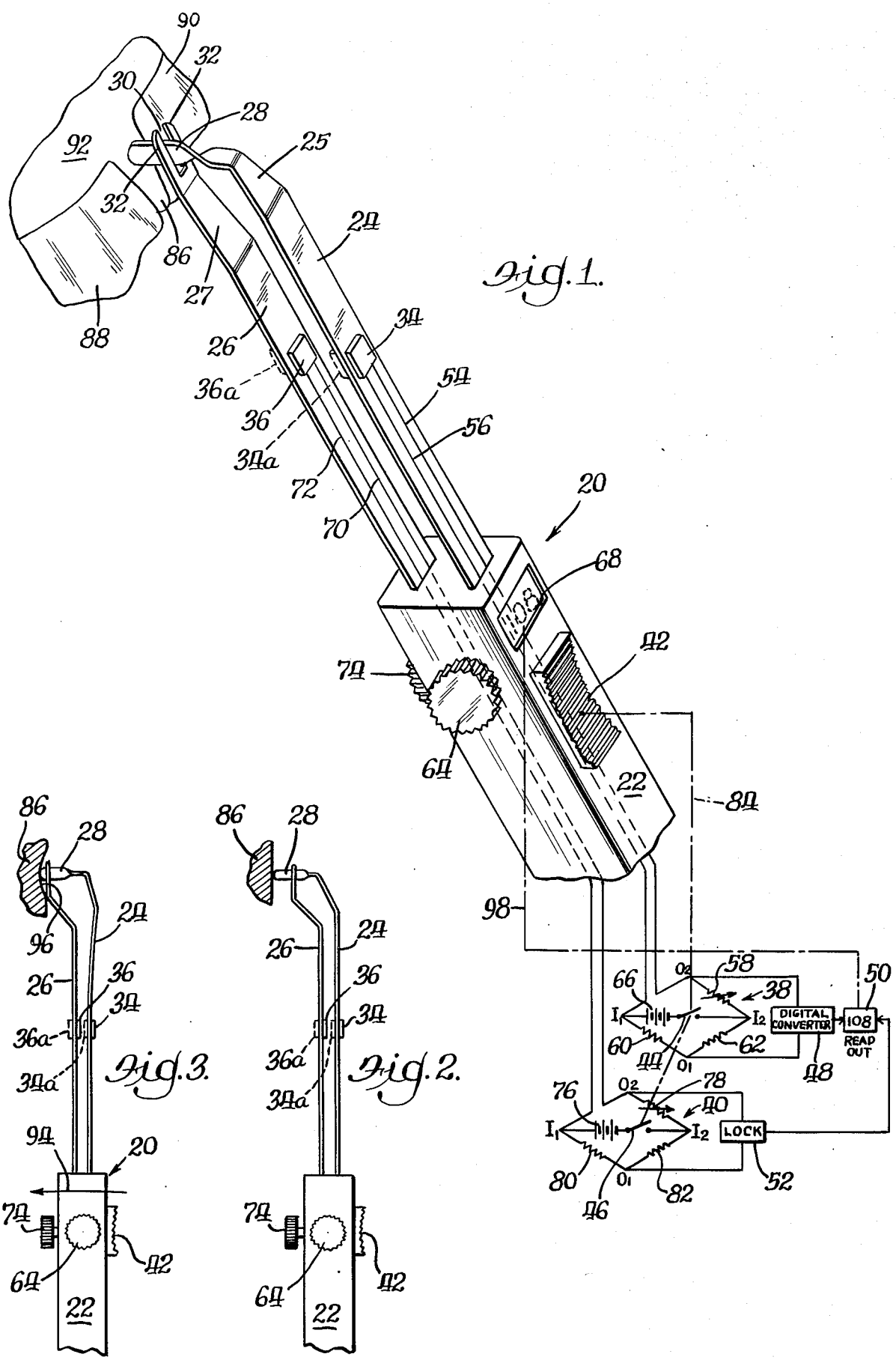

DUROMETER FOR INDENTIBLE TISSUE AND THE LIKE

BACKGROUND OF THE INVENTION

The invention belongs to the field of durometers which measure hardness of indentible tissue or material. The embodiment described is particularly useful in dental and medical practice for treating edema, swelling, puffiness, or distention of mouth or body tissues.

The most common complaint after removal of a mandibular third molar is swelling, which causes pain. In situations where tissues are required to be load-bearing, such as for dentures or artificial limbs, there is a great need for a reliable tool for mapping the tissue density and thickness over bone to aid in the equal distribution of force over the load-bearing area engaged by the denture or artificial limb. In the treatment of gum diseases such as gingivitis and pyorrhea, the gum and periodontal tissues become edemic, and swell and soften. As successful treatment proceeds, the swelling reduces and the tissues regain their normal healthy firmness.

Prior to the present invention, no satisfactory tool has been available for the accurate, repeatable, in vivo, measurement of the firmness of body tissues. In some cases, post-operative swelling of the cheek has been measured directly by means of a tape measurer or by callipers. In one method described in great detail in Int. J. Oral Surg. 1975: 4; pages 121-129 a photographic method following oral surgery is described but this is awkward, requiring the patient's head to be clamped in a fixed ring aligned with a camera. All these prior methods and apparatuses are imprecise at best, and fail to provide any very useful tissue measurements.

SUMMARY OF THE INVENTION

It is a general object of the present invention to provide a durometer tool which will give an accurate, repeatable measurement of hardness or firmness of body tissues and like materials.

Another object is to make the tool compact and readily usable in restricted spaces such as on periodontal (between teeth) tissue.

Another object is to make the tool readily portable, self-contained, self-powered, and having a digital read-out of tissue hardness which is automatically locked in the "On" position for as long as the operator needs it.

Other objects and advantages will be apparent from the following description taken in connection with the accompanying drawings in which:

BRIEF DESCRIPTION OF THE DRAWINGS

FIG. 1 is a fragmentary perspective view of a durometer employing the principles of the present invention with indicator and lock circuits which are normally contained within the handle, being shown diagrammatically externally thereof;

FIG. 2 is a side view of FIG. 1 at a somewhat reduced scale showing initial placement of the tool before making a tissue firmness measurement; and FIG. 3 is a view similar to FIG. 2 showing the final position of the tool in making a tissue firmness measurement.

Like parts are referred to by like reference characters.

DESCRIPTION OF THE PREFERRED EMBODIMENT

The improved durometer, generally designated 20, comprises a handle 22 having first and second parallel flexible beams 24 and 26 extending forwardly from it. Each flexible beam is a flat leaf spring.

The free end of the first beam 24 is bent to form an angular portion 25 and a right-angled tissue-engageable indentor 28 extending laterally from the beam past the free end of the second beam 26. The second beam is bent to form an angular portion 27 and is forked at its free end, having an open-ended slot 30 flanked by fingers 32, 32, through which the indentor extends.

First and second strain-sensing means comprising electrical strain gages 34 and 36 are bonded to the flexible beams 24 and 26 respectively. Alternatively, similar strain gages $34a$ and $36a$ may be bonded to the opposite sides of the beams, and either used with gages 34 and 36, or as substitutes for them. These may be of any type so constructed that strain in either beam is accompanied by a proportional change in some electrical characteristic of the gage, such as resistance, inductance or capacitance. Such strain gages are conventional and their construction and manner of bonding or cementing them to a body subject to strain are well-known, so will not be detailed here. Briefly, however, the strain gages 34 and 36 illustrated are of the resistance type which means that their electrical resistances change with flexing of the beams on which they are bonded.

In order to make use of such strain gages in the miniature sizes required for the present invention, they must be connected in some circuit for measuring very small changes in resistance. This is done conventionally by Wheatstone bridge circuits specifically designed for use with strain gages. They are well-known and readily available, together with analog (dial-type) or digital (numerical) read-out displays, so will not be detailed here. I prefer a digital read-out, as shown and described.

For a detailed discussion of all types of strain gages, the manner of bonding them to a body subject to strain, bridge control circuits, and read-out circuits and displays, reference may be had to "The Strain Gage Primer" by Perry and Lissner, published by McGraw Hill Book Co., Inc.

Briefly, the control system here is miniaturized sufficiently to fit entirely within the handle 22, making the tool completely self-contained and readily portable. Alternatively, the tool may be cable-connected to a console adjacent the work area or may be in communication by radio signals with a remote wall-mounted read-out display.

The system shown here, which is entirely self-contained in the handle 22 comprises a first bridge control circuit 38 for the first strain gage 34, a second bridge control circuit 40 for second strain gage 36, an On-Off switch control button 42 for first and second switches 44 and 46 in the bridge circuits, a digital converter 48, read-out display unit 50, and a lock circuit 52.

The first bridge circuit 38 has the usual four legs, with resistance strain gage 34 connected into one leg by conductors 54 and 56; the other three legs contain resistors 58, 60, and 62 connected as shown. Resistor 58 is variable, controlled by an adjustment wheel 64 on the side of the handle. A conductor, including a battery 66 and switch 44, is connected across input terminals $I_1$ and $I_2$. The digital converter 48 is connected across the output terminals $O_1$ and $O_2$. The digital converter is shown in block form and may be any conventional circuit for converting voltage from the bridge circuit 38 and transmitting them to read-out unit 50 to display a digital output visible through window 68 in the handle.

The second bridge control circuit 40 is similar, with resistance strain gage 36 shown connected into one leg via conductors 70 and 72, and resistors 78, 80, and 82 being connected in the other legs as shown. Resistor 78 is variable, controlled by an adjustment wheel 74 on the handle. A conductor, including battery 76 and On-Off switch 46, is connected across input terminals $I_1$ and $I_2$. The output from terminals $O_1$ and $O_2$ is fed to the lock circuit 52 which is, in turn, connected to the read-out unit 50. The lock circuit 52 may be any conventional circuit for locking or "freezing" the reading displayed in the read-out unit when strain gage 36 on the forked beam 26 changes its resistance in response to flexing of that beam, as for instance, when it touches the tissue being measured, and either begins to deflect, or deflects to an amount pre-determined by the adjustment of resistor 78.

Adjustment of the degree of flexure of the second or forked beam 26, before actuating the lock circuit 52, is important when working with different tissues. On extremely delicate or severely swollen and tender tissues such as gums or periodontal tissues, a minimum deflection will be appropriate. On other, normally harder tissues closely overlying bone structures, higher deflections may be preferred.

The button 42 is mechanically connected, within the handle, to the switches 44 and 46, by means not shown but indicated schematically by the broken line 84, so that forward movement of the button closes both switches simultaneously and rearward movement opens them.

Use and operation will now be described in one specific example, for measuring the firmness of periodontal tissue between molars 88 and 90 in gum 92.

First, the operator activates the tool by moving button 42 forward, thereby closing both switches 44 and 46. Wheel 64 is rotated to balance the first bridge control circuit 38, which is verified by a zero reading in window 68. Any similar adjustment of resistor 78 will be made by rotating wheel 74 if, in the opinion of the operator, a particular deflection of the forked beam 26 is desired to actuate the lock circuit 52.

To measure the hardness of the periodontal tissue 86, the operator then simply positions the tool as shown in FIGS. 1 and 2, and presses the handle in the direction of the arrow 94 (FIG. 3). As the indentor 28 presses into the tissue, making a small cavity 96 (FIG. 3), the indentor 26 will flex, changing the resistance of the strain gage 34. The degree of flexure, which is related to the hardness of the tissue, will be indicated by numerals of increasing value in window 68 as the indentor is pressed against the tissue. A high reading will indicate firmer tissue than a low reading. When the forked beam 26 contacts the tissue, as shown in FIG. 3, it will begin to flex. When it flexes sufficiently to the extent determined by the adjustment of resistor 78, a signal from bridge 38 will activate lock circuit 52 and thereby lock or "freeze" the reading in window 68. As shown, in the drawings, the reading is locked at the figure "108", this being shown in solid lines in the schematic circuit at the bottom of FIG. 1 and being repeated in broken lines within the window 68, both representations being interconnected by a broken line 98 to shown that these are the same. These readings may be calibrated to any customary scale used with durometers, or to some other scale considered more appropriate for body tissue measurements.

The above-described durometer is illustrative of a small number of many possible specific embodiments of the invention. Numerous and varied other arrangements and methods can readily be devised in accordance with the principles disclosed by those skilled in the art without departing from the spirit and scope of the invention.

The embodiments of the invention in which an exclusive property or privilege is claimed are defined as follows:

1. A durometer for indentible tissue and the like comprising:
    a movable handle having first and second spaced normally parallel flexible beams extending therefrom and terminating in free ends;
    the first beam having a tissue-engageable indentor;
    the second beam having a tissue engaging surface adjacent its free end;
    said indentor extending laterally from the free end of the first beam past the tissue engaging surface of the second beam when the beams are in such normally parallel relation;
    first sensing means for determining the magnitude of flexure of the first beam relative to the other beam when the indentor is pressed into tissue;
    indicator means operable in response to signals from the sensing means including read-out means for displaying readings and indicative of increasing magnitudes of flexure of the first beam by movement of the handle to press the indentor into tissue;
    second sensing means responsive to initial contact of the second beam with tissue adjacent the indentor to generate a lock signal; and
    lock means responsive to the lock signal to lock the reading displayed by the indicator means at the time of such initial contact of the second beam with tissue.

2. A durometer for indentible tissue and the like according to claim 1 in which at least the first sensing means includes an electrical strain gage.

3. A durometer for indentible tissue and the like according to claim 1 in which at least said second sensing means includes an electrical strain gage.

4. A durometer for indentible tissue and the like according to claim 1 in which said second sensing means includes means for generating said lock signal in response to a predetermined degree of flexure of said second beam beyond the point of initial contact with tissue.

5. A durometer for indentible tissue and the like according to claim 1 in which said second beam has an opening at the free end thereof through which said indentor extends into contact with the tissue.

6. A durometer for indentible tissue and the like according to claim 1 in which both said sensing means are electrical strain gages capable of changing their electrical characteristics in response to flexure of the respective beams;
    said indicator means operates in response to change of electrical characteristics of the strain gage on the first beam for displaying said readings indicative of flexure of said first beam;
    said lock signal is generated in response to change of electrical characteristics of the strain gage on the second beam when the second beam flexes a predetermined amount on contact with tissue; and battery means connected to said indicator means and to said lock means through On-Off switch means for controlling activation of both said indicator means and said lock means.

7. A durometer for indentible tissue and the like according to claim 6 in which said read-out means, battery means, and On-Off switch means, are within said handle.

8. A durometer for indentible tissue and the like according to claim 6 in which electrical bridge means are provided in said handle and are connected between said strain gages and said indicator means and lock means respectively.

9. A durometer for indentible tissue and the like according to claim 8 in which said handle has an externally adjustable member for adjusting the electrical characteristics of one element of said bridge means for balancing at least the portion of said bridge means between the strain gage on the first beam and the indicator means, and means for displaying the condition of balance of said bridge means in a window in said handle.

10. A durometer for indentible tissue and the like according to claim 9 in which said handle has another externally adjustable member for adjusting the electrical characteristics of one element of said bridge means for separately balancing at least the portion of said bridge means between the strain gage on the second beam and the lock means, for predetermining the flexure of said second means required to activate said lock means.

11. A durometer for indentible tissue and the like comprising:
a movable handle having first and second normally parallel movable beams extending therefrom comprising elestic means and terminating in free ends;
the first beam having a tissue-engageable indentor extending laterally from its free end past the free end of the second beam when the beams are in said normally parallel relation;
first sensing means for determining the magnitude of movement of the first beam relative to the handle when the handle is moved to press the indentor into tissue;
indicator means operable in response to signals from the sensing means including read-out means for displaying readings indicative of increasing magnitudes of movement of the first beam relative to the handle as the indentor is pressed into tissue;
second sensing means responsive to initial contact of the second beam with tissue adjacent the indentor to generate a lock signal; and
lock means responsive to the lock signal to lock the reading displayed by the indicator means at the time of such initial contact of the second beam with tissue.

12. A durometer for indentible tissue and the like according to claim 11 in which said second sensing means includes means for generating said lock signal in response to a predetermined degree of movement of said second beam relative to the handle beyond the point of initial contact with tissue.

13. A durometer for indentible tissue and the like according to claim 11 in which both said sensing means are elements capable of changing characteristics in response to movement of the respective beams;
said indicator means operating in response to change of said characteristics of the first sensing means for displaying said readings indicative of movement of said first beam; and
said lock signal is generated in response to change of said characteristics of the second sensing means when the second beam moves a predetermined amount on contact with tissue.

14. A durometer for indentible tissue and the like comprising:
a movable handle;
first and second tissue engageable members;
means for elastically mounting said members on the handle including a pair of beams connected at one end to the handle and each provided at its other end with a respective one of said members;
said beams each having a reference position to normally maintain a predetermined lateral spacing between them;
a first of said tissue engageable members comprising an indentor for pressing into tissue to be tested by movement of said handle and extending laterally from its beam past the other of the tissue engaging members when said beams are in said reference positions;
first sensing means for determining the magnitude of movement of the first beam relative to the handle when the handle is moved to press the indentor into tissue;
indicator means operable in response to signals from the sensing means including read-out means for displaying readings indicative of increasing magnitudes of movement of the first beam relative to the handle as the indentor is pressed into tissue;
second sensing means responsive to initial contact of the second member with tissue adjacent the indentor to generate a lock signal; and
lock means responsive to the lock signal to lock the reading displayed by the indicator means at the time of such initial contact of the second member with tissue.

15. A durometer according to claim 14 in which said second sensing means includes means for generating said lock signal in response to a predetermined degree of movement of said second beam relative to the handle beyond the point of initial contact with tissue.

16. A durometer according to claim 14 in which both said sensing means are elements capable of changing characteristics in response to movement of the respective beams.

* * * * *

UNITED STATES PATENT OFFICE
CERTIFICATE OF CORRECTION

Patent No. 4,132,224          Dated January 2, 1979

Inventor(s)     Robert G. Randolph

It is certified that error appears in the above-identified patent and that said Letters Patent are hereby corrected as shown below:

Column 3, Line 2, "voltage from" should be
-- voltage signals from--.

Column 3, Lines 51 and 52, "indentor 26" should be
--indentor beam 26--.

Column 6, Line 21, "pair of beams" should be
--pair of elongated beams--.

Signed and Sealed this

Third Day of April 1979

[SEAL]

Attest:

RUTH C. MASON
Attesting Officer

DONALD W. BANNER
Commissioner of Patents and Trademarks